(12) United States Patent
Taniguchi

(10) Patent No.: US 6,419,808 B1
(45) Date of Patent: Jul. 16, 2002

(54) HYDROCARBON SENSOR

(75) Inventor: Noboru Taniguchi, Osaka (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 0 days.

(21) Appl. No.: 09/539,317

(22) Filed: Mar. 30, 2000

(30) Foreign Application Priority Data

Apr. 1, 1999 (JP) .............................. 11-094934

(51) Int. Cl.[7] .......................................... G01N 27/407
(52) U.S. Cl. ...................... 204/424; 204/425; 204/426; 204/293; 205/787
(58) Field of Search .................... 204/293, 421, 204/424, 425, 426, 429; 205/787; 429/40

(56) References Cited

U.S. PATENT DOCUMENTS

| | | | | |
|---|---|---|---|---|
| 4,021,326 A | * | 5/1977 | Pollner et al. | 204/429 |
| 5,472,580 A | * | 12/1995 | Kennard, III et al. | 204/424 |
| 5,935,398 A | * | 8/1999 | Taniguchi et al. | 204/424 |
| 5,968,330 A | * | 10/1999 | Guth et al. | 204/424 |
| 6,030,909 A | * | 2/2000 | Fu | 501/10 |
| 6,090,249 A | * | 7/2000 | Guth | 204/421 |
| 6,238,535 B1 | * | 5/2001 | Taniguchi et al. | 204/434 |

FOREIGN PATENT DOCUMENTS

| | | |
|---|---|---|
| JP | 10-300718 | 11/1998 |
| JP | 11-337518 | 12/1999 |

OTHER PUBLICATIONS

"Function and Design of ZrO2 Exhaust Oxygen Sensors", pp. 2–1 through 2–7. Author and date unknown.*
"Limiting Current Sensor Using Proton Conduction Thin–Film", T. Inaba et al., Chemical Sensors, Japan Association of Chemical Sensors, vol. 11, Supplement B, pp. 145–148 (1995).
"Galvanic Cell Type Hydrocarbon Sensor Using a High–Temperature–Type Protonic Conductor", T. Hibino et al., Proceedings of the 61st Meeting of the Electrochemical Society of Japan, p. 99 (1994).

* cited by examiner

Primary Examiner—Robert J. Warden, Sr.
Assistant Examiner—Kaj K. Olsen
(74) Attorney, Agent, or Firm—Wenderoth, Lind & Ponack, L.L.P.

(57) ABSTRACT

A limiting-current-type hydrocarbon sensor of the present invention comprises a solid electrolyte formed of a barium-cerium-based oxide, capable of detecting hydrocarbon stably and accurately regardless of whether no oxygen is present or a high concentration of oxygen is present. The cathode on the surface of the solid electrolyte is formed of an alloyed layer including Au and Al. In particular, an alloyed layer including an Al—Au intermediate phase is suited for the alloyed layer of the cathode. The alloyed layer comprises a first layer including an Al—Au intermediate phase that is in contact with the surface of the solid electrolyte, and a second layer including a metal Al phase that covers the first layer. The Al phase of the alloyed layer blocks oxygen, and the Al—Au intermediate phase smoothens hydrogen association and reduces the resistance of the electrode. The hydrocarbon sensor can thus detect hydrocarbon accurately even when oxygen is included in an atmosphere.

16 Claims, 11 Drawing Sheets

HYDROCARBON SENSOR

FIELD OF THE INVENTION

The present invention relates to a hydrocarbon sensor for detecting hydrocarbon and measuring the concentration of the hydrocarbon in an atmosphere in the temperature range of ordinary temperature to high temperature (800° C.).

PRIOR ART

There are, in the art, known hydrocarbon sensors which are capable of detecting hydrocarbon in living environments, and in exhaust discharged from automobile engines, stoves and catalytic combustion apparatuses, which include catalytic converters or reformers, and are capable of being used for lean-burn control of combustion engines.

A method for measuring or detecting hydrocarbon has used a thin electrolytic substrate formed of a proton conductor as a solid electrolyte, i.e., a detecting medium. In this method, platinum electrodes are formed on both sides of the substrate so as to be opposite to each other, thereby forming a hydrocarbon sensor. Hydrocarbon in an atmosphere under measurement is dissociated into protons at the anode and the protons pass through the electrolytic substrate and reach the cathode, then causing the current or voltage to generate across both the electrodes which is detected.

An oxide-based proton conductor that can be heated and used at high temperatures over room temperature has been used for the electrolytic substrate to use such hydrocarbon sensors for combustion engines or other high-temperature apparatuses. In recent years, a calcium zirconate-based oxide having a composition of $CaZr_{0.9}In_{0.1}O_{3-\alpha}$ has been developed as the oxide-based proton conductor, and attempts have been made to apply the oxide to hydrocarbon sensors. For example, as a hydrocarbon sensor comprising a solid electrolyte formed of the calcium zirconium-based oxide, an electromotive-force-type sensor is disclosed by Hibino, Tanaki and Iwahara in the Proceedings of the 61st Conference (1994) of Electro-chemical Society of Japan, p99, in which Pd and Au electrodes are used on the main faces of the solid electrolyte.

Furthermore, a limiting-current-type sensor provided with a diffusion-determining portion made of porous alumina is disclosed by Inaba, Takahashi, Saji, Shiooka in the Proceedings of the 1995 Autumnal Conference (1995) of Japan Association of Chemical Sensors, p145.

Generally, in the limiting-current-type sensor, an anode made of platinum is disposed on one face of a thin electrolytic substrate having a proton conductivity, and a cathode made of platinum is disposed on the other face, so that the anode and the cathode are opposite to each other in contact with the substrate. The anode is provided with a diffusion-determining portion to transfer hydrocarbon molecules by diffusion from an atmosphere to the anode. The amount of the hydrocarbon to be diffused and moved to the anode surface is proportional to the partial pressure in the atmosphere to be measured. When the sensor is disposed in an atmosphere under measurement, and a constant voltage is applied across both electrodes, the hydrocarbon transferred by diffusion from the atmosphere to the anode is dissociated on the anode, whereby hydrogen ions, i.e., protons, are discharged into the electrolyte. The sensor can detect the amount of protons passing through the electrolytic substrate as a current flowing across the electrodes. The sensor uses the principle that the measured proton current is approximately proportional to the concentration of the hydrocarbon in the atmosphere.

However, the solid electrolyte made of the above-mentioned calcium-zirconium-based oxide has a low proton conductivity of about $5 \times 10^{-4}$ S/cm at 600° C. In order to raise the sensitivity of sensors, the operation temperature of the hydrocarbon sensor must be set at a high temperature of about 700° C. in the case of an EMF type-hydrocarbon sensor, or the solid electrolyte must be made thinner in a thin film in the case of a current-detecting-type hydrocarbon sensor. Otherwise, it is difficult to use the sensor because of low detection sensitivity. For these reasons, solid-electrolytic materials having higher proton conductivity have been demanded.

Furthermore, problems are also caused with respect to the detection mechanism and structure of the sensor. The EMF-type hydrocarbon sensor used conventionally cannot accurately detect hydrocarbon contents in an atmosphere in which no oxygen is present or the concentration of oxygen changes significantly, since the sensor utilizes the oxygen catalytic function of the electrode. The conventional limiting-current-type sensors comprising a diffusion-determining portion made of porous alumina have difficulty in setting the electrolytic voltage for electrolyzing hydrocarbon.

The inventors of the present invention have propose d a limiting-current-type (or constant potential electrolytic type) hydrocarbon sensor formed of a barium-cerium-based oxide having high proton conductivity in Japanese Patent Publication Kokai No. 10-300718. This sensor satisfactorily responds to hydrocarbon. Further, when no oxygen is present, the sensor can nearly linearly detect hydrocarbon in the range from the order of several ppm to several percents.

However, in the case where the concentration of hydrocarbon is very low (for example, 10 ppm or less) with no oxygen present in an atmosphere, it was found that when oxygen promptly enters from the outside, the detection output of the sensor increases. This is because the barium-cerium-based oxide has a characteristic of conducting oxide ions, whereby oxygen is taken into the electrolyte at the cathode, penetrating the electrolyte to the anode. To solve this problem, the inventors have developed a sensor wherein the cathode thereof is mainly made of metal Al to prevent the entry of oxygen at the cathode in Japanese Patent Publication No. 11-337518. The Al-containing metal cathode has a significant effect on reduction of the sensor output due to oxygen even when high levels of oxygen enter in the atmosphere.

However, in an application wherein this sensor is used to detect deterioration in the performance of a catalyst used to clean exhaust from automobile engines, when the catalyst deteriorates, the exhaust includes a high concentration of hydrocarbon (HC) and a considerably large amount of oxygen (about 2.5%) mixed with the hydrocarbon. If a sensor comprising a cathode made of Al and an anode made of Au is used for this kind of application, when the concentration of the oxygen in the exhaust becomes high (0.7 to 2.7% of $O_2$ in this example), the HC detection output of the sensor lowers as shown in FIG. 11, even though the exhaust includes a relatively high concentration of hydrocarbon (HC: 500 to 2000 ppmC), thereby causing another problem.

SUMMARY OF THE INVENTION

An object of the present invention is to provide a hydrocarbon sensor using a mixed ion conductive electrolyte which is capable of accurately measuring the hydrocarbon concentration even in an atmosphere containing high levels of oxygen, by preventing the change and reduction in HC detection current output at the time when such a high concentration of oxygen is mixed with the hydrocarbon atmosphere.

Another object of the present invention is to provide a hydrocarbon sensor comprising a cathode having a low electrode resistance.

The hydrocarbon sensor of the present invention comprises a solid electrolyte formed of a mixed ion conductor, an anode formed on one of surfaces of the electrolyte and a cathode formed on the other surface of the electrolyte, both opposed to each other, wherein the cathode is formed of an alloyed layer containing Al and a transition metal to be active to the hydrogen proton.

The transition metal is one or more elements selected from Groups 3 to 12 in the Periodic Table (IUPAC Inorganic Chemicals Nomenclatures (1989)). The transition metal may be preferably selected from active metals of Pt, Au, Ag, Cu, Pd, Mn, Fe, Ni, Co, and the like. Particularly, Au may be used as the transition metal, to provide an Al—Au alloy for an alloyed layer of the cathode.

For the cathode, a sintered layer, or a sintered film, may be used as an alloyed layer, which may be a solid phase or liquid phase containing Al and the transition metal. The alloyed layer of the cathode may include one or more of Al-transition metal intermediate phases, and, preferably, a metal Al phase together with the intermediate phases.

Especially, as the transition metal, Au may be used since the intermediate phases of Au and Al exhibit a property that dissociates protons into hydrogen and a property that prevents oxygen from converting into oxide ions, and also exhibit a considerably high electric conductivity required for the cathode.

The hydrocarbon sensor of the present invention does not detect current resulting from the conduction of oxygen through the electrolyte. The presence of the Al component in the cathode alloyed layer shields oxygen from the atmosphere from entering into the electrolyte by preventing the oxygen from being ionized at the cathode.

For the use of Au, even if a higher concentration of oxygen is present together with hydrocarbon in the atmosphere to be measured, the Au in the alloyed layer prevents oxidation of the cathode, and effectively prevents an increase in cathode resistance due to the oxidation of the electrode. The similar effects are provided in the transition metals by Cu, Ag, Ni, Co, Pt, Pd and other noble metals.

Furthermore, the Au component does not hinder the hydrogenation of protons, thereby preventing reduction of the proton detection current. In particular, the Au component in the cathode accelerates the association reaction of protons from the solid electrolyte at the cathode, thereby accelerating the discharge of hydrogen at the cathode. As a result, the hydrocarbon sensor of the present invention can have high hydrocarbon detection performance even when a high concentration of oxygen becomes promptly included in the atmosphere, for example, in automobile exhausts, under measurement.

For producing a hydrocarbon sensor comprising a cathode formed of this kind of alloyed layer, first paste mainly containing Au is applied to an electrolytic substrate to form a film, and the film is fired to form an Au film. Next, another paste mainly containing Al is applied to the Au film on the substrate and fired to form an alloyed layer which can be used as the cathode. By sintering, the alloyed layer comprises a first layer containing an Al—Au intermediate phase which makes contact with the substrate and a second layer including a metal Al phase which covers the first layer.

Another method of producing the hydrocarbon sensor may be used in which paste mainly containing Au and Al is applied to an electrolytic substrate to form a film, which is then fired to form an alloyed layer including Au and Al. The paste may be prepared of a mixture of powders of metals Au and Al. The alloyed layer is used as the cathode. This method may provide an alloyed layer including one or more of Al—Au intermediate phases, or an alloyed layer including Al—Au intermediate phases dispersed in a metal Al phase.

BRIEF DESCRIPTION OF THE DRAWINGS

The invention is explained in further detail with reference to the accompanying drawings, in which.

DETAILED DESCRIPTION OF THE INVENTION

Figure 1A:
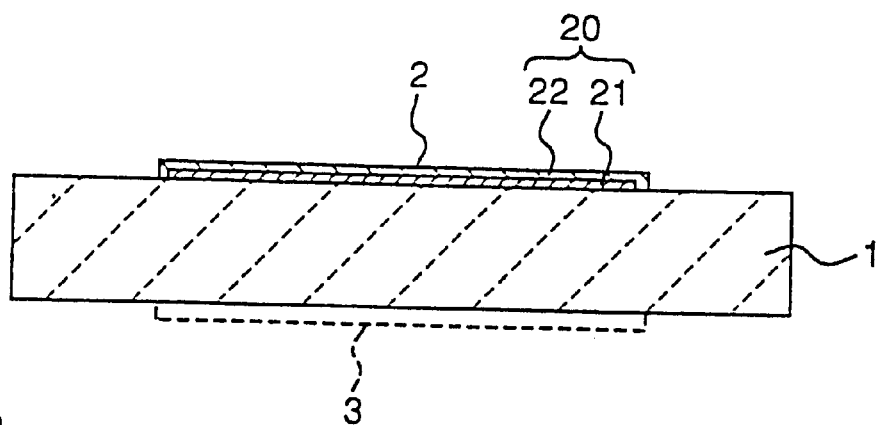
FIG. 1A is a view showing the structure of a cathode formed on a solid substrate for a hydrocarbon sensor in accordance with the present invention.

The hydrocarbon sensor in accordance with the present invention comprises a solid electrolyte formed of a proton conductor. Generally, oxides having high conductivity to protons also have high conductivity to oxide ions. The solid electrolyte of the present invention is formed of a mixed-ion conductor, i.e., a proton type-oxide-ion type conducting electrolyte. Such an electrolyte may preferably be formed of a Ba—Ce-based oxide which is high in sensitivity of hydrocarbon and which has high conductivity to oxide ions together with protons.

The solid electrolyte is formed as a thin substrate, and electrodes are formed on both sides of the substrate, one electrode on each side. The cathode is formed of an alloyed layer containing Al and a transition metal to be active to the hydrogen to proton (excluding Al).

The transition metal is one or more elements selected from Groups 3 to 12 in the Periodic Table(IUPAC Inorganic Chemicals Nomenclatures (1989)). The transition metal may be preferably selected from the metals of Pt, Au, Ag, Cu, Pd, Mn, Fe, Ni, Co, and the like. These metals exhibit the properties to discharge protons into hydrogen and at the same time, to activate oxygen to ions.

In the preferable embodiment of the invention, Au may be used as the transition metal, to provide an Al—Au alloy layer having an advantageous effect on the non-sensitivity to the presence of oxygen, as will described below, for an alloyed layer of the cathode. Therefore, in the preferred embodiment invention, the cathode formed of an Au—Al alloyed layer will be explained.

Au is alloyed with Al to form Al—Au intermediate phases, as described below. These intermediate phases are hardly reactive with oxygen in an atmosphere at temperatures up to 900° C., whereby the cathode is not involved in the ionization of the oxygen from the atmosphere. Advantageously, the intermediate phases have considerably high electric conductivity.

In the present invention, it is preferable that Al in the cathode alloyed layer may be present as a metal Al phase or an Al—Au intermediate phase, and that Au in the cathode alloyed layer is present as any of Al—Au intermediate phases. However, it is not preferable that Au is exposed to the cathode surface as a metal Au phase (including an solid solution of Au wherein Al is dissolved). This is because the metal Au activates oxygen to ions on the surface of the cathode, thereby moving the oxide ions to the electrolyte. As a result, oxygen ion current as well as proton current is detected across the electrodes, thereby causing output errors.

Preferably, the alloyed layer for the cathode may preferably contains 4 to 90 wt % Al and 10 to 96 wt % Au based on the total weight of Au and Al in the alloyed layer. If the Al content is more than 90 wt %, because of less amount of $Al_2Au$, the cathode will have higher electric resistance and lose the sensitivity of hydrocarbons under high oxygen conditions in the atmosphere. On the other hand, if the Al content is lower than the 4 wt %, a free Au phase, i.e., a Au solid solution, appears with any Al—Au intermediate phase in the alloyed layer and readily may react to the oxygen in the atmosphere, adversely affecting the output current from the sensor due to the presence of the oxygen.

Such an alloyed layer of the above composition may include both a metal Al phase and an Al—Au intermediate phase, as a first type of alloyed layer. In this type, the alloyed layer including both the metal Al phase and an $Al_2Au$ phase can be taken as an example.

In a second type of the alloyed layer, Al and Au may be present in the form of one, two or more Al—Au intermediate phases. Examples of the Al—Au intermediate phases may include $Al_2Au$, AlAu, $AlAu_2$, $Al_2Au_5$, $AlAu_3$ and $AlAu_4$. Even if any of Al—Au intermediate phase is used solely without metal Al phase included, the Al—Au intermediate phase can effectively shield oxygen by preventing the ionization of oxygen, thereby keeping the cathode conductive and hydrogenating protons from the solid electrolyte being emitted into the atmosphere.

As shown in FIG. 1A, the alloyed layer of the above-mentioned cathode 2 may preferably comprise a first layer 21 including an Al—Au intermediate phase in contact with a solid electrolyte 1, and a second layer 22 including a metal Al phase covering the first layer 21.

In use of the hydrocarbon sensor, the metal Al phase of the second layer 22 makes contact with an atmosphere and can block oxygen in the atmosphere from the electrolyte. The Al-Au intermediate phase of the first layer 21 makes contact with the surface of the solid electrolyte, whereby the cathode 2 offers conductivity so as to function as an electrode and hydrogenates protons.

This alloyed layer of the cathode can be formed as a sintered layer formed of the liquid or solid phases containing separately metals Au and Al.

The sintered layer may be formed by applying a first layer mainly containing Au on the solid electrolyte and a second layer mainly containing Al on the first layer, and then sintering both layers to be alloyed, whereby an Al—Au intermediate phase is formed in the sintered layer.

A method of producing the hydrocarbon sensor of the present invention will be described below. First, a paste mainly containing Au is applied to an electrolytic substrate to form a film, and the film is fired to form an Au film. Thereafter, a paste mainly containing Al is applied to the Au film and fired to form an alloyed layer which is used as the cathode. As a result, the cathode comprises a first layer including an Al—Au intermediate phase in contact with the surface of the solid electrolyte and a second layer including a metal Al phase covering the first layer.

Another form of the alloyed layer including both the metal Al and the Al—Au intermediate phase takes the form of particles of the Al—Au intermediate phase dispersed in the metal Al phase. Another form of the alloyed layer may be one or more Al—Au intermediate phases but not containing any metal Al phase.

Such an alloyed layer of the cathode can be formed as a sintered layer formed of the liquid or solid phases based on Au and Al. In this case, the alloy may preferably be produced by sintering a mixture of powders of metals Au and Al to make a sintered layer in which both Al phase and the Al—Au intermediate phase can also be included.

Such a sintered alloyed layer for the cathode can be provided by applying a paste mainly containing Au and Al to the electrolytic substrate to form a Au—Al containing film, baking the substrate to remove the binder mixed in the film and then firing the film at suitable temperatures to make the sintered layer.

In the present invention, pastes are used containing a mixture of particles or flakes of one of more metals, such as, for example, Au and/or Al, and an organic binder such as thermosetting resins. The pastes with proper viscosity are applied on the substrate surface of the solid electrolyte to form a thin pasted film, and are then often dried to cure the resin to obtain the dried, hard film. Often, the pasted films are heated to about 80 to 120° C. to promote the curing reaction of the binder. Then, the cured film, which contains metal powders of flakes and resin, is fired at sintering temperatures sufficiently to sinter the metal components, for example, in the case of Au—Al alloyed layer from the Al and Au mixed powder in the paste, about 800 to 900° C. or up to 1000° C. for 0.5 to 5 hours or more. In this temperature range, Al melts to react to the Au on the substrate to make a melt and/or Al—Au intermediate compounds such as $Al_2Au$, and, during cooling, the Al—Au intermediate compound and, in the case of an unduly amount of Al, the residue of an Al phase. Thus, the Al—Au alloyed layer is formed on the substrate and is used for a cathode of the sensor.

In raising the sintering temperature until the sintering occurs, a bake-out step may be provided for oxidizing and/or volatilizing the resin component to deposit the residual metal components on the substrate surface. In the bake-out step the pasted film is held at 300 to 500° C.

For the solid electrolyte in the present invention, a Ba—Ce-based oxide represented by a conventional formula of $BaCeO_{3-\alpha}$, may be used since it has high proton conductivity. In particular, it may be used as a sintered body represented by $BaCe_{1-x}Ln_xO_{3-\alpha}$ wherein part of Ce may be replaced with another rare earth element Ln. Gadolinium Gd is preferably used as a rare earth element.

Figure 1B:
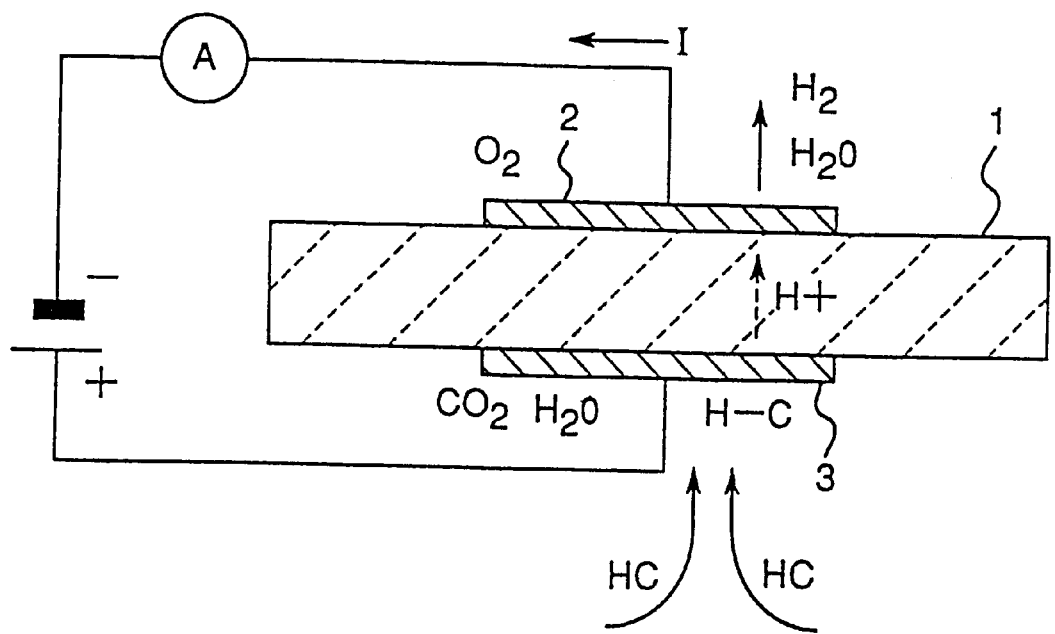
FIG. 1B is a schematic sectional view showing a current-detection-type hydrocarbon sensor.
Figure 6:
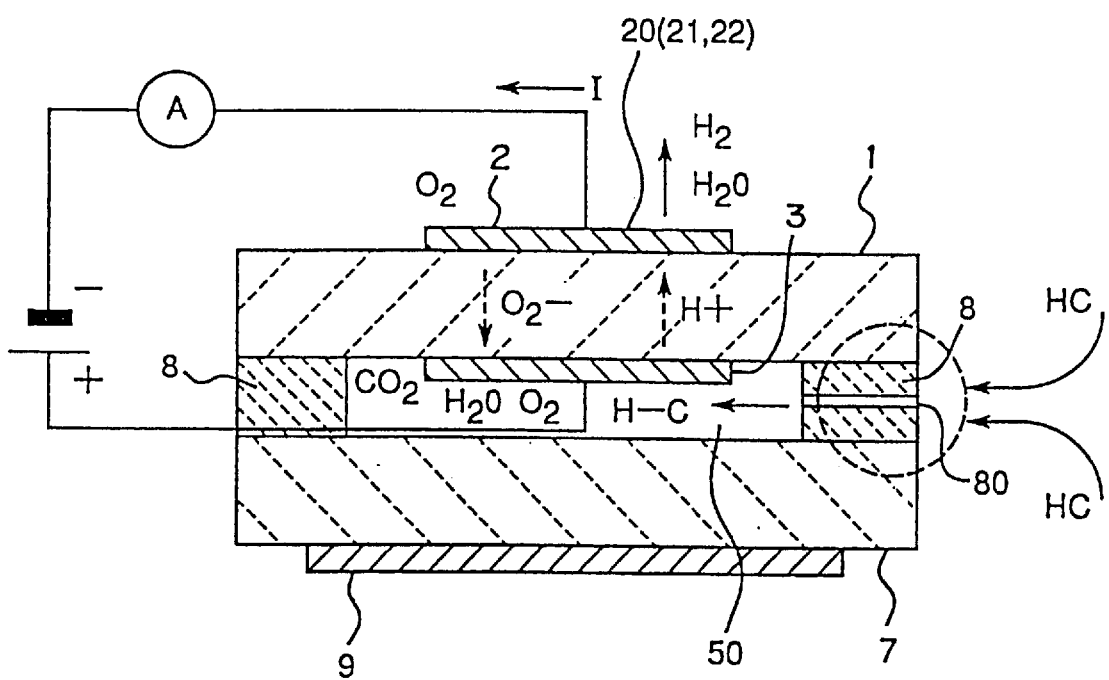
FIG. 6 is a sectional view showing a limiting-current type hydrocarbon sensor in accordance with a third embodiment of the present invention.

In the hydrocarbon sensors of the present invention shown in FIGS. 1B and 6, a solid substrate 1 is a thin sintered body formed of a Ba—Ce-based oxide. A cathode 2 is formed of the above-mentioned alloyed layer 20 on one side of the substrate 1 while an anode 3 is formed on the other side of the substrate 1 oppositely to the cathodes respectively, thereby forming two electrodes.

The hydrocarbon sensors of the present invention may use the conventional anodes such as a film of one or more of active metals of Pt, Au, Ag, Cu, Pd, Mn, Fe, Ni, Co, or the like, having a decomposition catalysis function for hydrocarbon.

In the structure of the solid electrolytic substrate provided with the cathode and anode, a series connection comprising a DC power supply and an ampmeter is connected between the cathode and the anode as shown in FIG. 1B.

The hydrocarbon sensor of this invention can preferably be utilized as a current-detection-type hydrocarbon sensor. As shown in FIG. 6, in order to use this structure as a current-detection-type hydrocarbon sensor, a hydrocarbon diffusion-determining portion is provided on the side of the anode 3 of the solid electrolytic substrate 1 provided with the cathode 2 and the anode 3 on the sides thereof, one electrode on each side. The diffusion-determining portion is constituted by attaching a ceramic substrate 7 to the electrolytic substrate 1 via an inorganic adhesive layer 8 so as to provide a hermetically sealed space around the anode 3, thereby to form an anode compartment 50. In this example, the inorganic adhesive layer 8 is provided with a diffusion determining hole 80 which passes through the adhesive layer 8 to provide gas passage between the atmosphere and the anode compartment 50, thereby allowing hydrocarbon to diffuse therebetween through the hole 80.

This limiting-current-type sensor utilizes proton conductive limiting current for linearly detecting the concentration of hydrocarbon. The hydrocarbon in an atmosphere in which the sensor is placed diffuses through the diffusion-determining hole 80, to enter the anode compartment 50 and reach the anode 3. The hydrocarbon having reached the anode 3 is dissociated into protons by electrolysis on the surface of the anode under a suitable voltage applied between the anode and cathode as shown in FIG. 6. The protons are conducted through the solid electrolytic substrate 1 under the applied voltage, and discharged as hydrogen at the cathode. At this time, a current flows depending on a moving amount of the protons through the substrate, and a limiting current is generated depending on the amount (concentration) of the hydrocarbon determined by the diffusion.

Furthermore, in the hydrocarbon sensor mentioned above, preferably, a lead that includes a composition of Au and Al similar to the cathode may be connected to the cathode, to take out cathode current, by the above alloyed layer.

EMBODIMENTS

Embodiment 1

The present embodiment is an example of hydrocarbon sensors comprising a solid electrolytic substrate of a Ba—Ce-based oxide, and a cathode of an alloyed layer comprising a first layer mainly containing Au in contact with one surface of the solid electrolytic substrate and a second layer mainly containing Al and covering the first layer.

In current-detection-type hydrocarbon sensors shown in FIG. 1B, as the solid electrolyte 1 a thin sintered substrate is used having a composition of $BaCe_{0.8}Gd_{0.2}O_{3-\alpha}$ and measuring 10 mm×10 mm in size and 0.45 mm in thickness. An Al—Au alloyed layer is used for the cathode 2 (active electrode), and the anode 3, the opposite electrode (reference electrode) to the cathode, is a platinum electrode.

To make the cathode, Au paste ("N2764 Paste" made by Tanaka Kikinzoku Kogyo K. K.) and Al paste ("9203C Paste" made by Noritake Co., Ltd.) were applied to the electrolytic substrate by using screen printing technique. First, the Au paste was screened to the surface of the solid electrolyte 1 to produce an Au pasted film 21, and fired at 850° C to make an electrode layer. The Al paste was screened on the Au film such that the Al pasted film may cover the Au film and fired at 850° C. for 1 hour to sinter into an Al—Au based alloyed layer 20.

To evaluate the sensors produced as above, prototypes were examined as to whether it functioned as a hydrocarbon sensor by using an actual automobile engine. The sensors were provided in an automobile exhaust pipe immediately on a downstream side from a cleaning catalytic apparatus. In the experiment, a sensor was heated and maintained at a temperature of 640±30° C., and then a voltage of 1.2 V was applied between the cathode and the anode (cathode is negative voltage). The exhausting gas is passed through the pipe with variably changing concentrations of hydrocarbons, while the output current of the sensor was measured.

In addition, in the case that a catalyst was deteriorated completely, a sensor was provided inside a pipe with no catalytic devise in which high concentrations of oxygen would be present. As described above, the concentration of hydrocarbon was variably changed, and the output of the sensor was examined.

Figure 2:
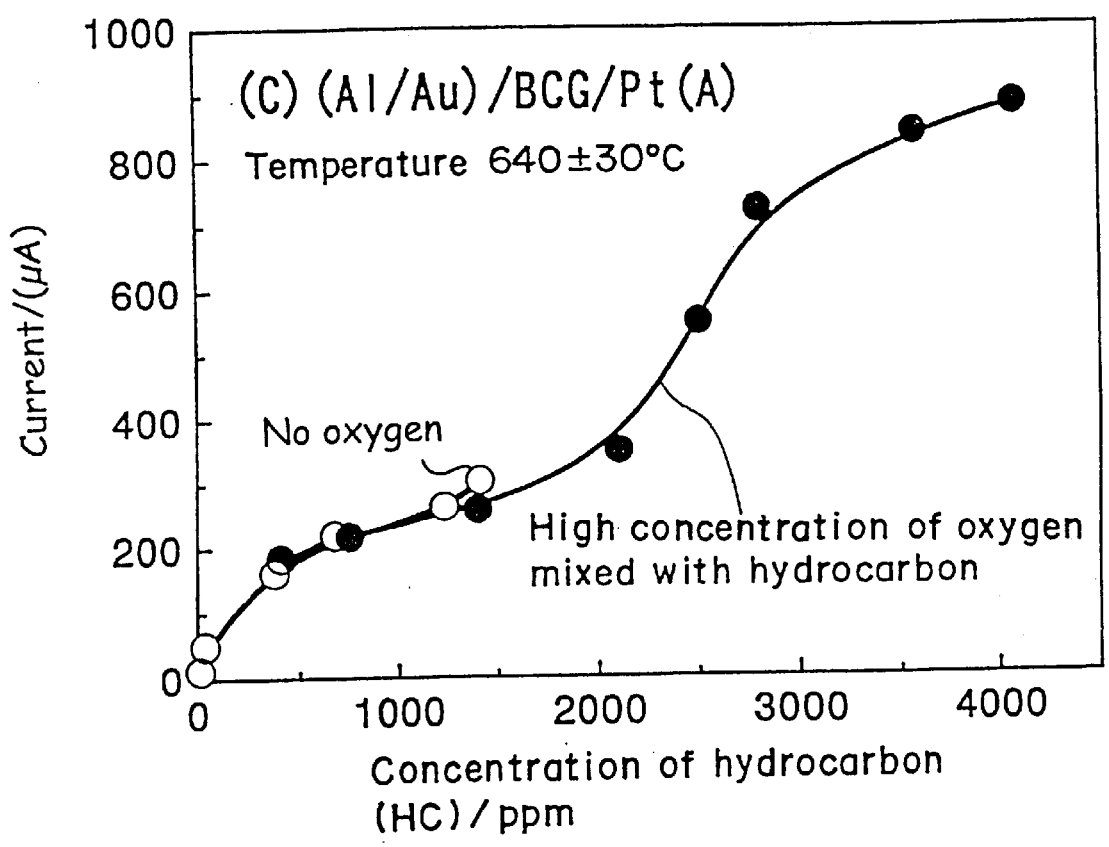
FIG. 2 is a graph showing the relationship between the concentration of hydrocarbon in an engine exhaust pipe and the output current of a hydrocarbon sensor in accordance with a first embodiment of the present invention.
Figure 11:
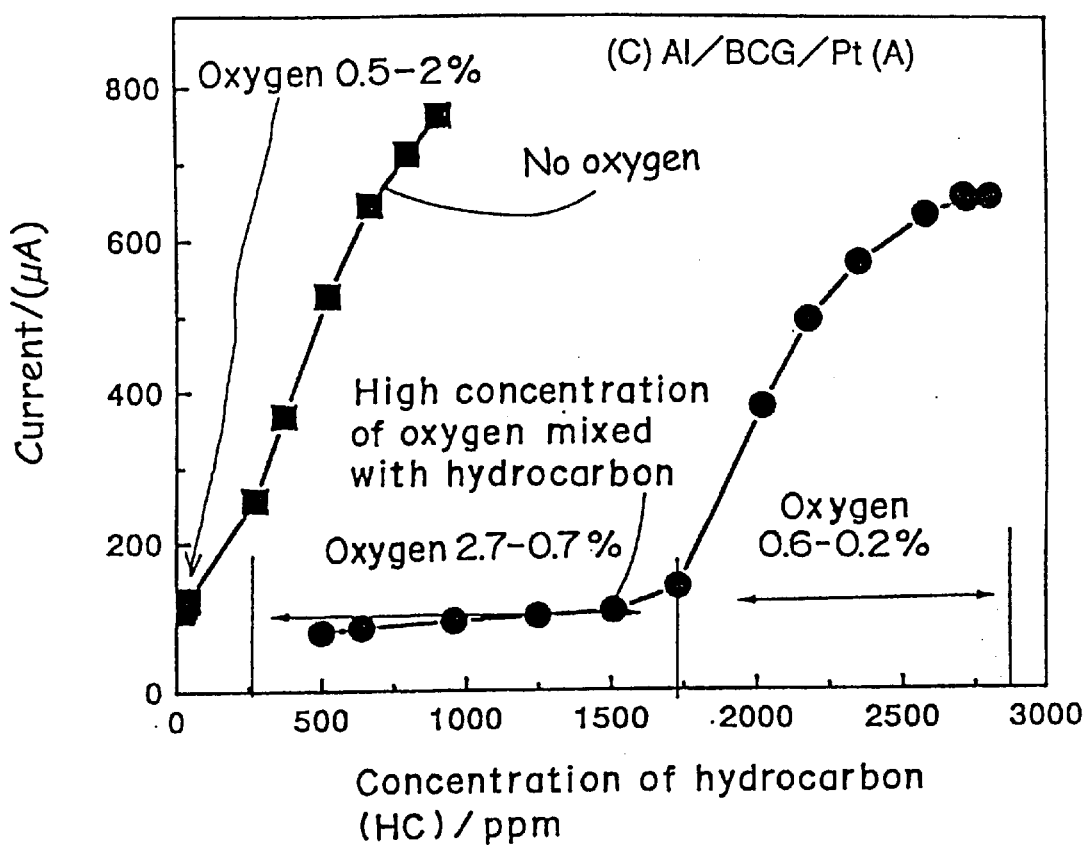
FIG. 11 is a graph showing the relationship between the concentration of hydrocarbon in an engine exhaust pipe and the output current of a conventional hydrocarbon sensor.

FIG. 2 is a graph showing the relationship between the concentration of hydrocarbon and the output current of the sensor in the case where a catalytic devise is provided and oxygen was eliminated thereby. FIG. 2 also shows the case where no catalytic devise was provided and a high concentration of oxygen is mixed with hydrocarbon in the exhausting atmosphere. The output of the sensor of the present embodiment can increase depending on the hydrocarbon concentrations in the exhausting gas that do not include oxygen, and is substantially identical to that in the case of the exhausting gas containing high concentration of oxygen with the hydrocarbon. On the other hand, the conventional sensor in which a cathode is formed of platinum as well as the anode, as shown in FIG. 11, the output current from the sensor is lowered as a high concentration of oxygen was mixed with hydrocarbon.

It is thus found t hat the sensor of the present invention can accurately detect hydrocarbon even when a high concentration of oxygen is pre sent together with hydrocarbon, and that the sensor has a high detection capability even when a high concentration of oxygen is mixed with hydrocarbon.

Figure 3:
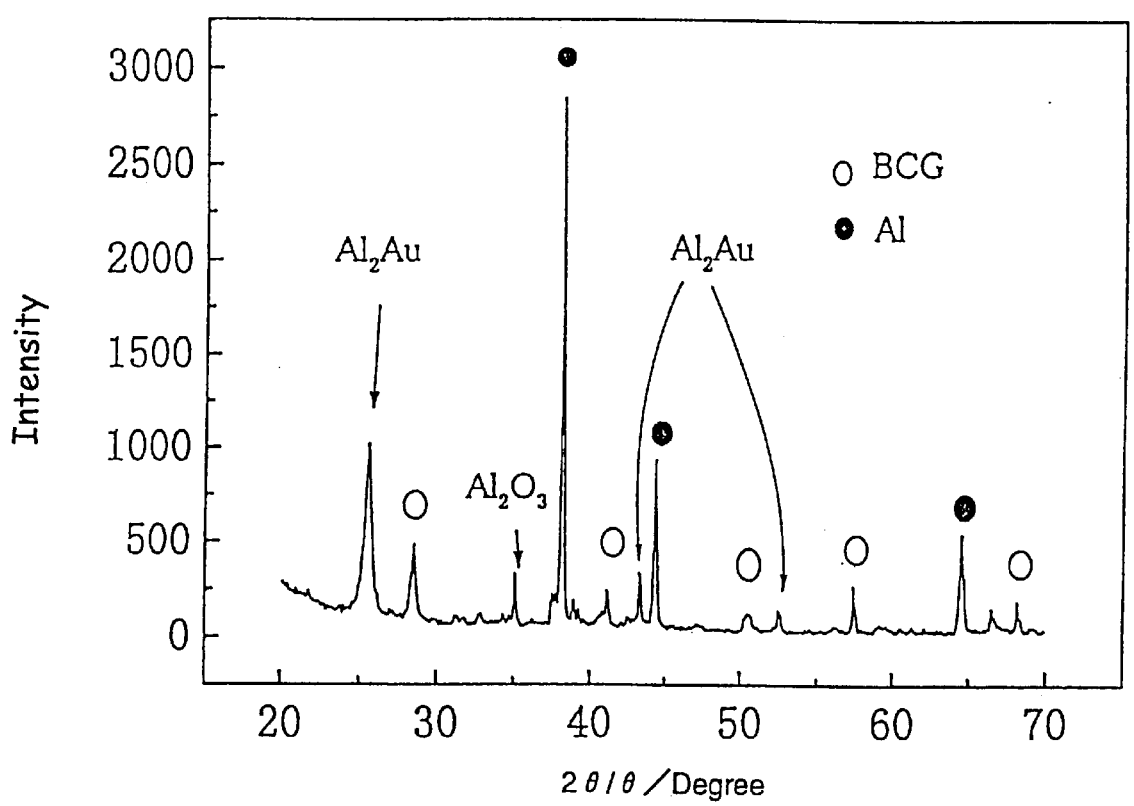
FIG. 3 is a chart showing the X-ray diffraction of the Al—Au alloyed layer of the cathode used for a hydrocarbon sensor in accordance with the first embodiment of the present invention.

FIG. 3 is a chart showing the X-ray diffraction of the alloyed layer of the cathode. It is found through the diffraction chart that while a part of Al has been oxidized to alumina, another part of Al is present in the form of a metal Al phase, and that an $Al_2Au$ intermediate phase is produced by the reaction of Au and Al. It is therefore believed that Al, in the Al pasted film, reacts with Au in the Au pasted film while the films are being fired. As such, the cathode 2 on the substrate 1 is formed of an alloyed layer, which comprises the first layer 21 containing the Al—Au intermediate phase on the surface of the solid electrolyte, and the second layer 22 including the metal Al phase and covering the first layer as shown in FIG. 1A.

In this cathode having a sintered layer, it is found that the first layer includes an Al-Au intermediate phase under the second layer of aluminum.

Embodiment 2

In this embodiment, an alloyed layer having mixed phases, including Au and Al, is provided for the cathode as follows. A paste was prepared in which Al and Au are mixed to screen print as a single pasted film.

First, the Au paste was mixed with the Al paste in a volume equal ratio. This mixed paste was screened onto the electrolyte as described above to form a film of 8 μm in thickness and fired at 850° C. for 1 hour to form a single alloyed layer, and at the same time a Pt electrode also was fired as the anode, i.e., a reference electrode, to produce a hydrocarbon sensor.

Figure 4:
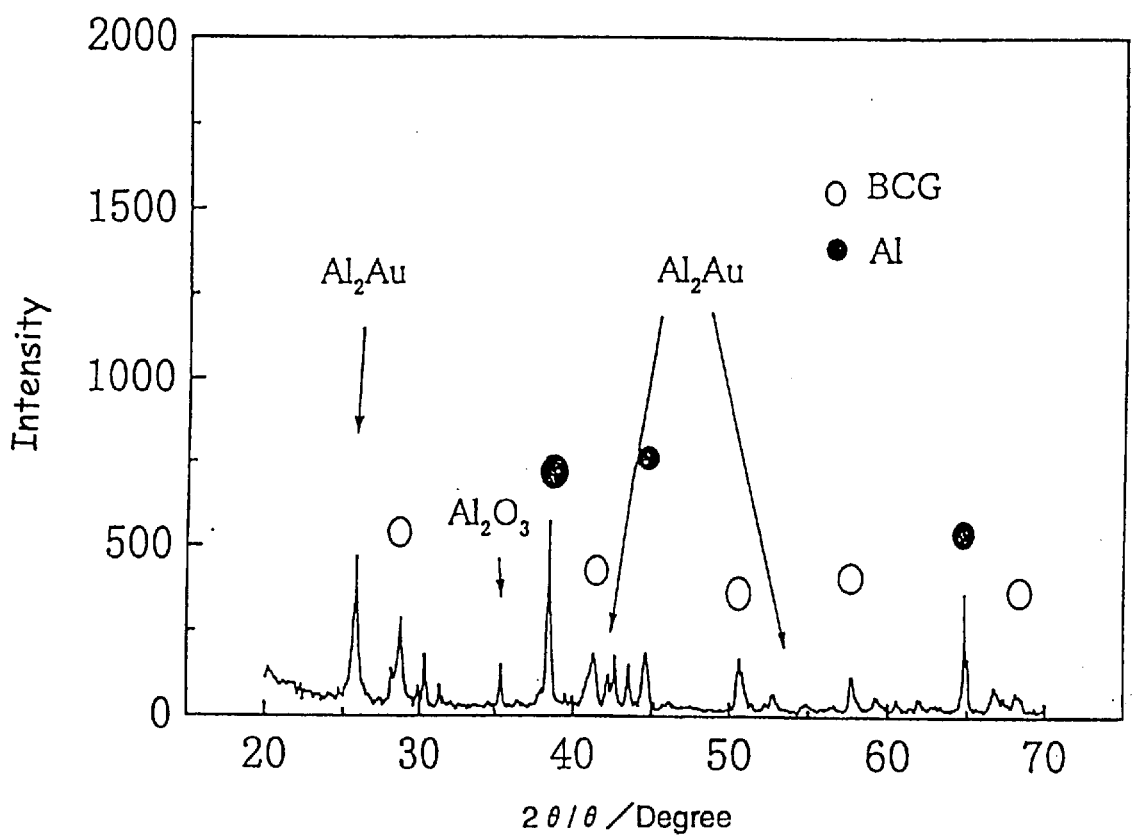
FIG. 4 shows a X-ray diffraction chart of an alloyed layer of a cathode with mixed phases that include Au and Al, and used for a hydrocarbon sensor in accordance with a second embodiment of the present invention.

After baking, the composition of the alloyed layer of the cathode was examined by X-ray diffraction. As the result of the examination, an Al phase and an $Al_2Au$ phase were observed, as shown in FIG. 4.

Experiments were conducted to confirm that an Al—Au alloyed layer electrode blocked oxygen, smoothened hydrogen association and reduced the resistance of the electrode, and that hydrocarbon was detected accurately even when a high concentration of oxygen was present.

Figure 5:
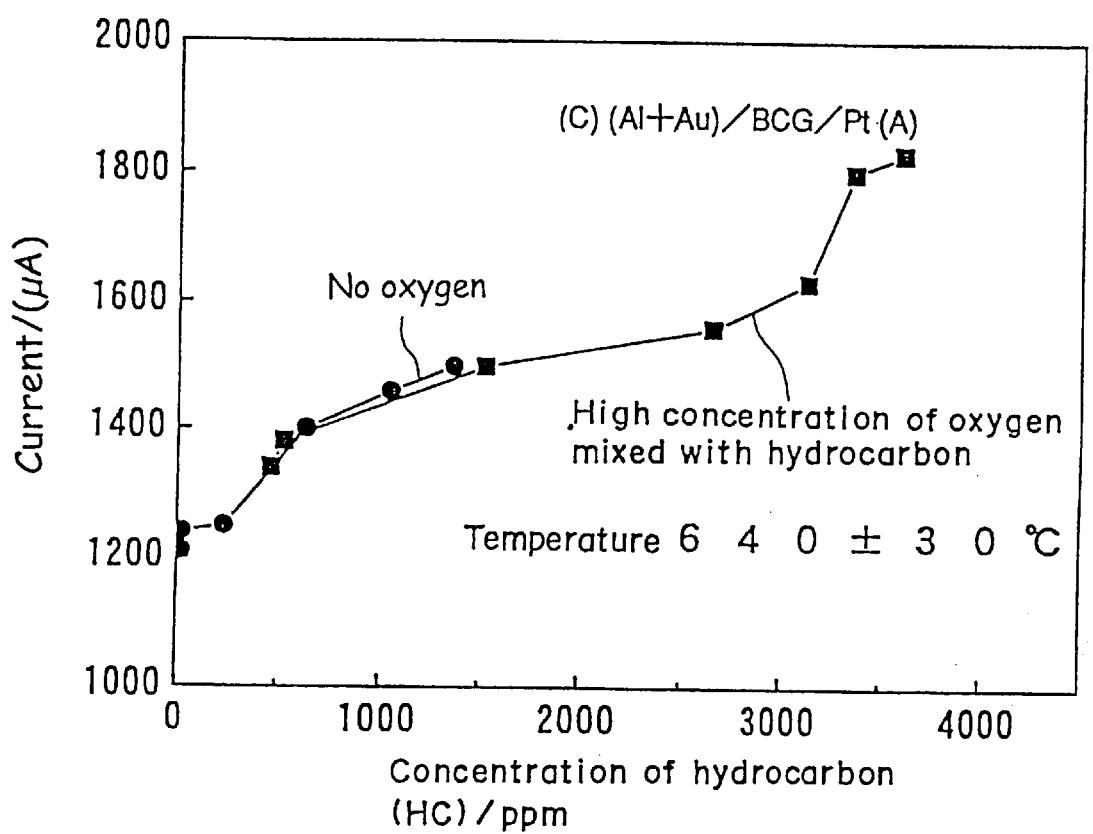
FIG. 5 is a graph showing the relationship between the concentration of hydrocarbon in an engine exhaust pipe and the output current of a hydrocarbon sensor in accordance with the second embodiment of the present invention.

As the above-mentioned embodiment 1, by using actual engine exhaust, the characteristics of the hydrocarbon sensor were determined depending on whether a catalyst was present or not. FIG. 5 shows the relationship between the hydrocarbon (HC) concentration in the atmosphere and the output current of the sensor. The output current of the sensor depending on the hydrocarbon concentration in the atmosphere where no oxygen was present was nearly identical with that in the case when a high concentration of oxygen was mixed with hydrocarbon in the atmosphere. As a result, it can be seen that the presence of an $Al_2Au$ compound in a alloyed layer of the cathode can effectively prevent oxygen penetration into the solid electrolyte, smoothen the association of protons to hydrogen which may easily release toward the atmosphere, and reduce resistance of the electrode, and also that the hydrocarbon concentration can accurately be detected by this sensor even in the presence of oxygen in a high level.

Embodiment 3

The present embodiment shows an example of a limiting-current-type hydrocarbon sensor. Referring to FIG. 6, a solid electrolyte 4 is formed of a sintered substrate having a composition of $BaCe_{0.8}Gd_{0.2}O_{3-\alpha}$ and measuring 10 mm×10 mm in size and 0.45 mm in thickness. An anode 3 made of platinum is disposed on the surface of the sintered substrate 1. A cathode 2 is formed of a sintered body obtained by overlaying Al layer on an Au—Al layer with contact to the substrate. A hydrocarbon diffusion-determining portion is provided on the anode side, comprising an inorganic adhesive layer 8 is for med on the surface of the solid electrolyte a round the anode 3 and a ceramic substrate 7 covering the end. A heater 9 is attached to the ceramic substrate 7 to heat the sensor to a desired temperature at the time of measurement.

To prepare the cathode, Au paste ("TR206 Paste" made by Tanaka Kikinzoku Kogyo K. K.) and Al paste ("9203C Paste" made by Noritake Co., Ltd.) were applied to the electrolytic substrate by screen printing just as in the case of Embodiment 1. First, the Au paste was applied and fired at 850° C. for 1 hours to form an Au layer as a first layer. The Al paste was applied to the Au layer and fired at 850° C. for 1 hour.

As shown in Embodiment 1, to carry out evaluation, a prototype sensor produced as described above as was examined as to whether it functioned as a hydrocarbon sensor by using it in an actual automobile engine. The sensor was heated at a temperature of 640±30° C. using the heater 9, and a voltage of 1.2 V was applied across the cathode and anode (cathode is applied with negative voltage). The sensor was equipped in the exhausting duct of the engine where the hydrocarbon concentration in automobile exhaust was variably changed, and a sensor was examined immediately on the downstream side from a cleaning catalytic device in the duct through which the exhaust had passed. In addition, in the case where the catalyst was deteriorated completely, a sensor was also examined under a condition having no catalyst where the concentration of oxygen was high.

Figure 7:
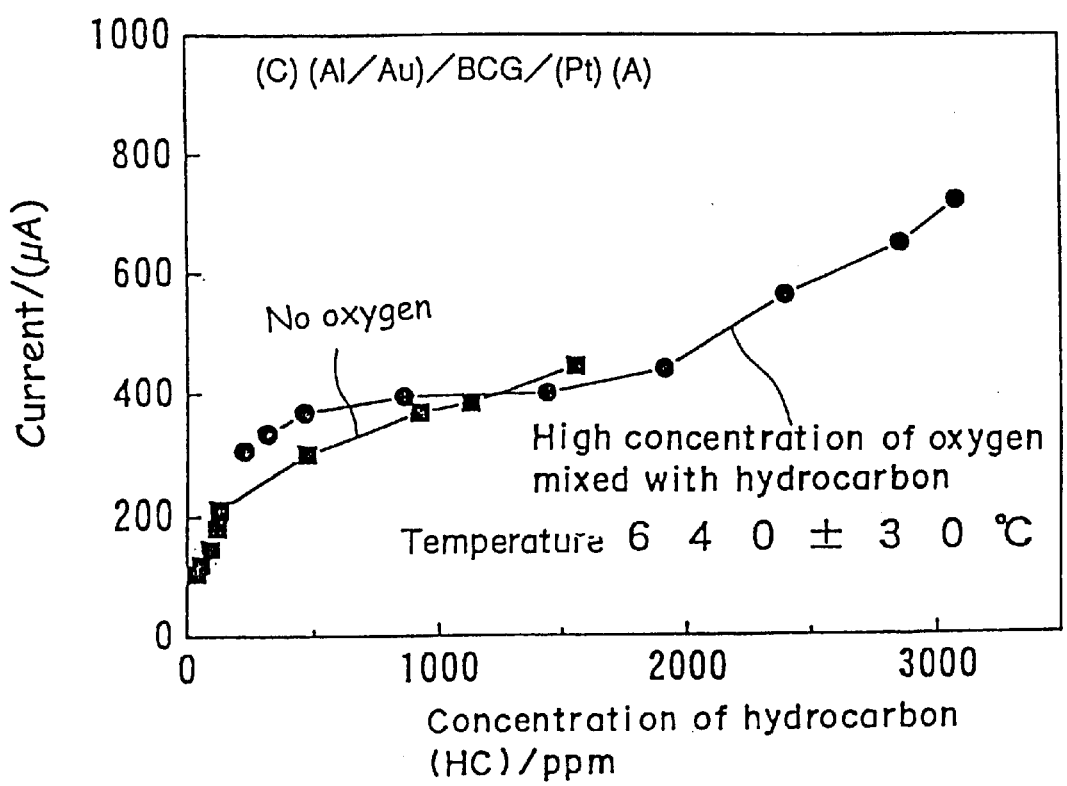
FIG. 7 is a graph showing the relationship between the concentration of hydrocarbon in an engine exhaust pipe and the output current of a hydrocarbon sensor in accordance with the third embodiment of the present invention.

FIG. 7 is a graph showing the relationship between the concentration of hydrocarbon and the output current of the sensor, in the case of the exhausting gas containing no oxygen with a catalyst and in the case of the exhausting gas containing high oxygen levels of 0.4 to 2.7% in the exhausting atmosphere without a catalyst. The sensor of the present embodiment gradually increases in output current depending on the concentration of hydrocarbon and substantially causes no difference between the case of an absence of oxygen and the case of high oxygen content. In comparison with the output current of the conventional sensor as shown in FIG. 11, having lowered when a high concentration of oxygen is mixed with hydrocarbon, it is found that the sensor of the present invention can accurately detect the concentration of hydrocarbon with less dependency on the oxygen content of the atmosphere.

Furthermore, as shown in the case of the preceding embodiment, another experiment was conducted to confirm that the sensor comprising the Al—Au alloyed layer electrode was able to accurately detect the concentration of hydrocarbon even when a high concentration of oxygen entered into the atmosphere. An Au—Al containing paste was prepared such that the Au paste was mixed with the Al paste in a volume ratio of 1:2, both pastes being the same as that used in Embodiment 1. This Au—Al containing paste was applied to the electrolyte by screen printing as described above and fired at 850° C. and at the same time, a Pt electrode was formed in the baking as a reference electrode and thus produce a hydrocarbon sensor.

Figure 8:
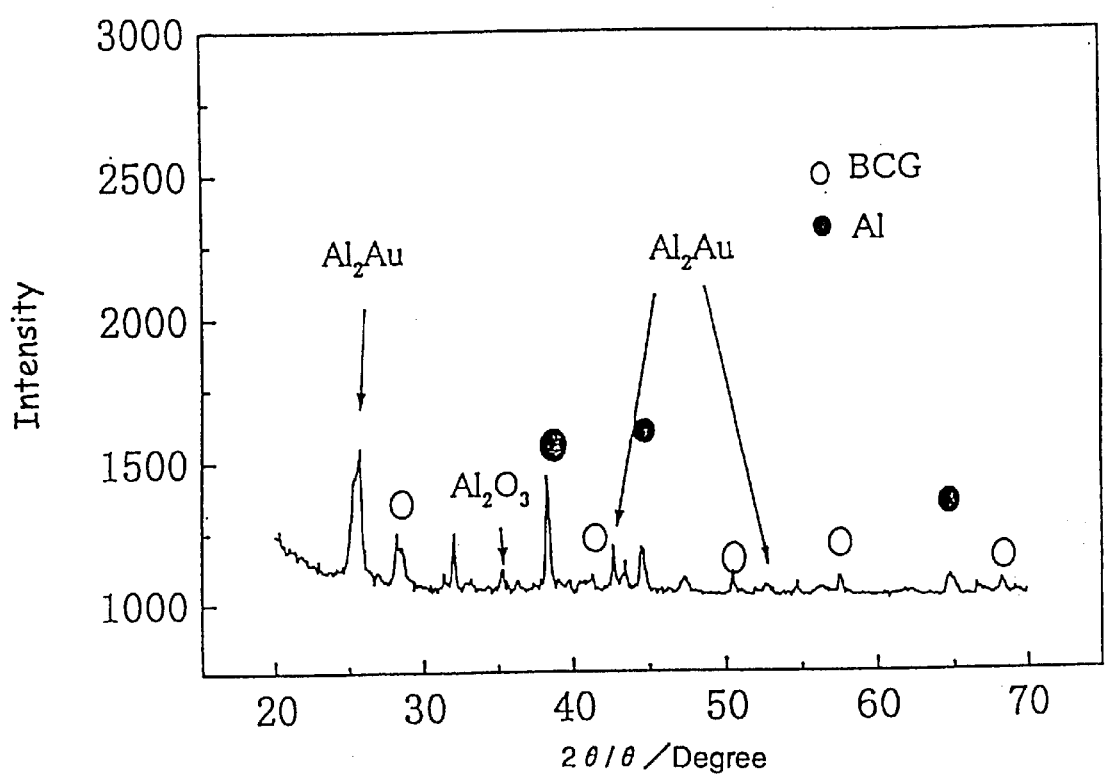
FIG. 8 is a chart showing the X-ray diffraction of an Al—Au alloyed layer used for a hydrocarbon sensor in accordance with the third embodiment of the present invention.
Figure 9:
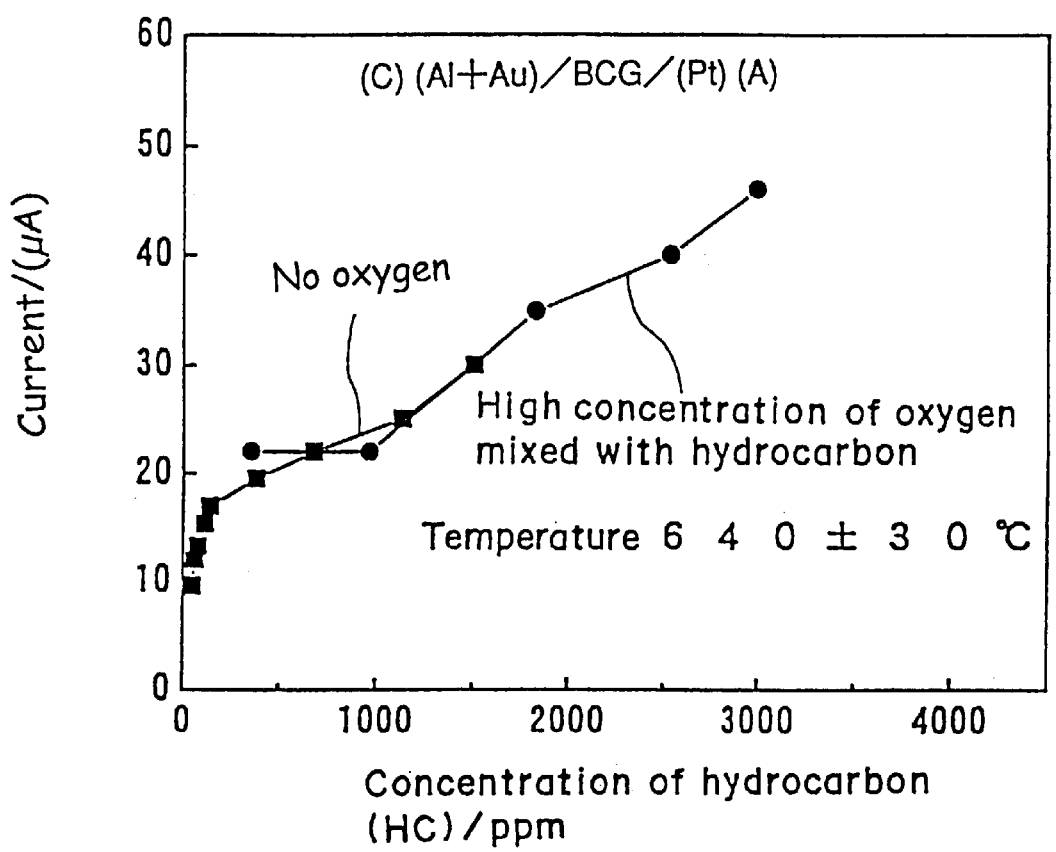
FIG. 9 is a graph showing the relationship between the concentration of hydrocarbon in an engine exhaust pipe and the output current of a hydrocarbon sensor in accordance with the third embodiment of the present invention.

The composition of the alloyed layer, which was obtained after the mixed paste was fired, was examined by X-ray diffraction and, as the result of the examination, an $Al_2Au$ intermediate phase was observed mainly as shown in FIG. 8. By using an actual engine, in the same way as described above, the characteristic of the hydrocarbon sensor was examined in the case of no oxygen in the exhausting gas when engine exhaust passed through a catalytic device, and in the case of high levels of oxygen when engine exhaust did not pass through a catalytic device. As shown in FIG. 9, the output current of the sensor depending on the concentration of hydrocarbon was constant regardless of whether no oxygen present or whether a high level of oxygen was mixed with hydrocarbon. Consequently, it was found that in the limiting-current-type sensor, the alloyed layer of the cathode, including the $Al_2Au$ phase, can effectively prevent oxygen penetration to the electrolyte, promote hydrogen association and reduce the resistance of the electrode. Thus, by using the alloyed layer as the cathode, the concentration of hydrocarbon can be detected accurately even when a high concentration of oxygen is present.

Embodiment 4

This embodiment is an example of a hydrocarbon sensor comprising a solid electrolyte formed of a Ba—Ce-based oxide, a cathode of Al—Au alloyed layer, and an adhesive to connect a lead to the cathode to lead the cathode current to outer connections being also formed of the alloyed layer including Au and Al.

For the experiment, after fabricating the cathode of electrodes of Al—Au alloyed layer and the anode of Pt layer on the substrate in the same manner as embodiment 3, an adhesive for the lead was attached on the cathode using two materials. The first material for the adhesive conventionally being of Pt and Au. The other adhesive for the lead was formed of an Al—Au alloyed layer, as used for the present embodiment. Then, leads made of Au were connected to the attached adhesive layer in the cathode and the anode on the other side. In the same way as the preceding embodiments, by using an actual engine, the characteristic of the hydrocarbon sensor was examined in the presence and absence of oxygen at the measuring points of hydrocarbon in the exhausting duct.

Figure 10:
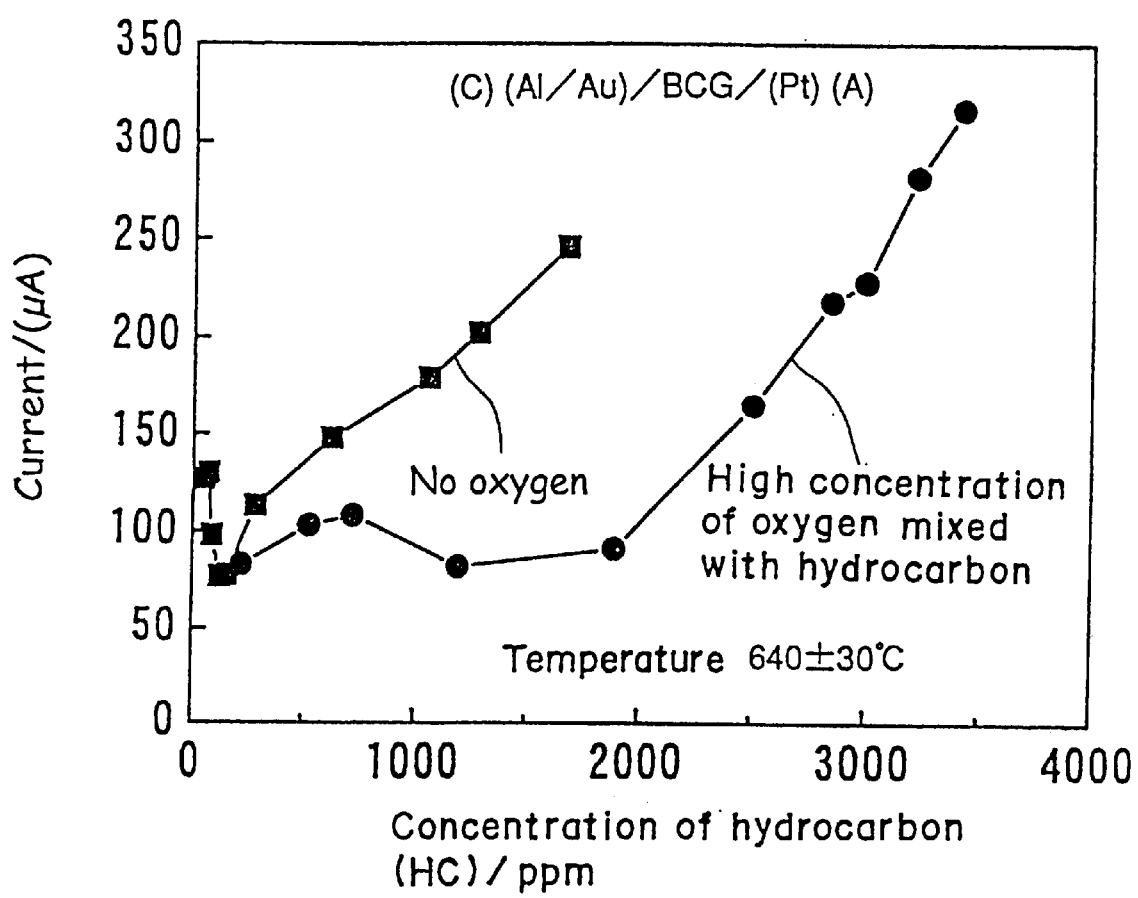
FIG. 10 is a graph showing the relationship between the concentration of hydrocarbon in an engine exhaust pipe and the output current of a hydrocarbon sensor in accordance with a fourth embodiment of the present invention comprising a lead adhesive formed of conventional Pt paste.

In the conventional sensor comprising the lead adhesive including Au and Pt, the output current of the sensor drifted with respect to the hydrocarbon content in the exhausting atmosphere as a result of the presence of oxygen. The response of the sensor to oxygen is shown in FIG. 10. This means that the lead adhesive also may act as a cathode at the portion where the adhesive makes contact with the cathode. The Au and Pt in the adhesive easily dissociates oxygen molecules from the atmosphere to cause a current to flow due to the oxide ions detected.

However, in the present embodiment, comprising the lead formed of an Al—Au alloyed layer, the drift of the sensor output due to the oxygen level and the response of the sensor to oxygen were not observed. As a result, it is determined that a highly reliable sensor can be produced by using a lead adhesive layer formed of an Al—Au alloyed layer.

What is claimed is:

1. A hydrocarbon sensor of a current-detecting type comprising:
    a solid electrolyte substrate formed of a proton-oxide ion mixed conductor, said substrate having a first major surface and a second major surface;
    an anode attached on the first major surface of said substrate;
    a cathode attached on the second major surface of said substrate, such that the cathode is opposed to the anode; and
    an external constant-voltage power source being operable to apply a constant voltage across, and measure a current flowing between, the anode and the cathode;
    wherein the anode and the cathode are connected in series to the external constant-voltage power source; and
    wherein the cathode is formed of an alloyed layer containing Al and one or more of transition metals in Groups 3 to 12 in the Periodic Table.

2. The hydrocarbon sensor according to claim 1, wherein the one of the transition metals is Au.

3. The hydrocarbon sensor according to claim 2, wherein the alloyed layer of the cathode is a sintered layer including Au and Al.

4. The hydrocarbon sensor according to claim 3, wherein the alloyed layer of the cathode comprises a sintered layer, the sintered layer comprising:
    a first layer containing Au, the first layer being in contact with the solid electrolyte; and
    a second layer containing Al, the second layer covering the first layer.

5. The hydrocarbon sensor according to claim 4, wherein the sintered layer of the cathode has an Al—Au intermediate phase obtained by sintering the first and second layers.

6. The hydrocarbon sensor according to claim 2, wherein the alloyed layer of the cathode comprises a sintered body including mixed powder of Au and Al, and an Al—Au intermediate phase.

7. The hydrocarbon sensor according to claim 2, further comprising:
    an anode compartment enclosing the anode;
    wherein the solid electrolyte comprises a diffusion-determining portion operable to diffuse the gas to the anode compartment enclosing the anode.

8. The hydrocarbon sensor according to claim 2, further comprising a lead formed of another alloyed layer containing Au and Al in contact with the cathode for introducing cathode current.

9. The hydrocarbon sensor according to claim 1, wherein the alloyed layer of the cathode includes an Al—Au intermediate phase.

10. The hydrocarbon sensor according to claim 9, wherein the Al—Au intermediate phase includes at least one of $Al_2Au$, $AlAu$, $AlAu_2$, $Al_2Au_5$, $AlAu_3$ and $AlAu_4$.

11. The hydrocarbon sensor according to claim 9, wherein the alloyed layer of the cathode includes a metal Al phase in the presence of the Al—Au intermediate phase.

12. The hydrocarbon sensor according to claim 9, wherein the alloyed layer of the cathode comprises:
    a first layer including an Al—Au intermediate phase in contact with the surface of the solid electrolyte; and
    a second layer including a metal Al phase which covers the first layer.

13. The hydrocarbon sensor according to claim 12, wherein the Al—Au intermediate phase includes at least one of $Al_2Au$, $AlAu$, $AlAU_2$, $Al_2Au_5$, $AlAu_3$ and $AlAu_4$.

14. The hydrocarbon sensor according to claim 1, wherein the solid electrolyte is a barium-cerium-based oxide including a rare earth element other than Ce as a third metal element.

15. The hydrocarbon sensor according to claim 14, wherein the rare earth element is gadolinium.

16. The hydrocarbon sensor of a current-detecting type according to claim 1, wherein said first major surface comprises a hydrocarbon diffusion-determining portion, the hydrocarbon diffusion-determining portion comprising:
    a ceramic substrate placed over the anode;
    an inorganic adhesive layer that seals the solid electrolyte substrate to the ceramic substrate;

an anode chamber surrounding the anode, the anode chamber being surrounded by the solid electrolyte substrate and the ceramic substrate; and a diffusion determining hole communicating between the anode chamber and an outside atmosphere, the diffusion determining hole operable to diffuse atmospheric gas into the anode chamber from the outside atmosphere.

* * * * *